United States Patent
Smolarz

(10) Patent No.: US 11,110,118 B2
(45) Date of Patent: Sep. 7, 2021

(54) FORMULATIONS FOR TREATING ACID REFLUX COMPRISING SODIUM ALGINATE

(71) Applicant: PHARAGEN LLC, Las Vegas, NV (US)

(72) Inventor: Joseph Ryan Smolarz, Charlotte Amalie, VI (US)

(73) Assignee: PHARAGEN LLC, Las Vegas, NV (US)

( * ) Notice: Subject to any disclaimer, the term of this patent is extended or adjusted under 35 U.S.C. 154(b) by 0 days.

(21) Appl. No.: 16/289,242

(22) Filed: Feb. 28, 2019

(65) Prior Publication Data
US 2019/0269717 A1 Sep. 5, 2019

Related U.S. Application Data

(60) Provisional application No. 62/637,551, filed on Mar. 2, 2018.

(51) Int. Cl.
| | | |
|---|---|---|
| *A61K 31/734* | (2006.01) | |
| *A61K 33/10* | (2006.01) | |
| *A61K 9/16* | (2006.01) | |
| *A61K 9/48* | (2006.01) | |
| *A61P 1/04* | (2006.01) | |
| *A61K 9/00* | (2006.01) | |

(52) U.S. Cl.
CPC .......... *A61K 31/734* (2013.01); *A61K 9/0095* (2013.01); *A61K 9/1617* (2013.01); *A61K 9/485* (2013.01); *A61K 9/4858* (2013.01); *A61K 9/4875* (2013.01); *A61K 33/10* (2013.01); *A61P 1/04* (2018.01)

(58) Field of Classification Search
None
See application file for complete search history.

(56) References Cited

U.S. PATENT DOCUMENTS

| | | | |
|---|---|---|---|
| 4,140,760 A | 2/1979 | Withington | |
| 2007/0087038 A1* | 4/2007 | Richardson | .......... A61K 9/0065 |
| | | | 424/439 |
| 2008/0317855 A1* | 12/2008 | Jolliffe | ................ A61K 9/5015 |
| | | | 424/466 |
| 2015/0020712 A1 | 1/2015 | Wosylus et al. | |

FOREIGN PATENT DOCUMENTS

| | | | | |
|---|---|---|---|---|
| CA | 2474520 C | * | 4/2012 | ............. A61K 33/00 |
| WO | WO-9511668 A1 | * | 5/1995 | ........... A61K 9/0065 |

OTHER PUBLICATIONS

Definition of "medication administration" from the Free Dictionary Medical Dictionary. Downloaded Jul. 29, 2020 from https://medical-dictionary.thefreedictionary.com/medication+administration (Year: 2020).*
Kim, Hee Man. "Raft formation of sodium alginate in the stomach." Journal of neurogastroenterology and motility, (2016), vol. 22, No. 4: 705-706.
Kwiatek, Monika A., et al. "An alginate-antacid formulation (Gaviscon Double Action Liquid) can eliminate or displace the postprandial 'acid pocket' in symptomatic Gerd patients." Alimentary pharmacology & therapeutics, (2011), vol. 34, No. 1: 59-66.
Sylvester, Deborah C., et al. "Chronic cough, reflux, postnasal drip syndrome, and the otolaryngologist." International journal of otolaryngology, (2012), vol. 2012: 1-6.
International Search Report PCT/US2019/020060 dated Apr. 29, 2019.
Abbas et al.,"pH Responsive Alginate Plymetric Rafts for Controlled Release by Using Box Behnken Response Surface Design", Designed Monomers and Polymers, vol. 20, No. 1, 2017, pp. 1-9.

\* cited by examiner

*Primary Examiner* — Michael P Cohen
(74) *Attorney, Agent, or Firm* — McBee Moore & Vanik, IP, LLC

(57) ABSTRACT

The disclosure provides for pharmaceutical compositions comprising an alginate salt, such as sodium alginate. The disclosure further provides for processes and methods for making pharmaceutical compositions. In yet a further aspect, the disclosure provides for methods of utilizing a pharmaceutical composition for treatment of acid reflux diseases. In another aspect, the disclosure provides for formulations suitable for oral use in dosage forms of capsules and dry powders.

21 Claims, No Drawings

FORMULATIONS FOR TREATING ACID REFLUX COMPRISING SODIUM ALGINATE

CROSS-REFERENCE PARAGRAPH

This application is a U.S. Non-Provisional Application which claims priority to U.S. Provisional Application No. 62/637,551, filed Mar. 2, 2018. The disclosure of the priority application is incorporated in its entirety herein by reference.

FIELD

The disclosure provides for pharmaceutical compositions comprising an alginate salt, such as sodium alginate. In another aspect, the disclosure provides for methods of utilizing a pharmaceutical composition for treatment of acid reflux diseases. In another aspect, the disclosure provides for formulations suitable for oral use in dosage forms of capsules and dry powders. The disclosure further provides for processes and methods for making pharmaceutical compositions described herein.

BACKGROUND

Approximately one-quarter of the Western population exhibit symptoms of gastroesophageal reflux disease (or "GERD") on at least a weekly basis. In fact, GERD is among the most frequent reasons for outpatient gastroenterology consultation.

GERD is a digestive disorder that affects the lower esophageal sphincter, the ring of muscle between the esophagus and stomach. GERD is characterized by the return of the stomach's contents back up into the esophagus. In normal digestion, the lower esophageal sphincter opens, allowing food to pass into the stomach, and closes to prevent food and acidic stomach contents from flowing up and into the esophagus. GERD occurs when the lower esophageal sphincter is weak or relaxes inappropriately, thereby allowing the stomach's contents to flow upward and into the esophagus.

Individuals with GERD commonly suffer from heartburn caused by the acidic stomach contents. More than 60 million Americans suffer from heartburn at least monthly, and more than 15 million adults suffer from heartburn on a daily basis.

Laryngopharyngeal reflux (or "LPR") is another common reflux disease, which is characterized by stomach acid backing up into the back of the pharynx or larynx, or even into the back of the nasal airway. This reflux of acid can cause inflammation in areas not protected against gastric acid exposure. Unlike GERD, heartburn is not typically associated with LPR, and thus LPR is commonly referred to as "silent reflux."

Stomach acid that accumulates and pools in the throat and larynx can cause long-term irritation and damage. Without treatment, such damage can be severe. In infants and children, irritation and damage caused by LPR can result in narrowing of the area below the vocal cord, contact ulcers, recurrent ear infections caused by problems with eustachian tube function, and lasting buildup of middle ear fluid. In adults, silent reflux can scar the pharynx and larynx and can increase risk of cancer in the area, affect the lungs, and may aggravate conditions such as asthma, emphysema, or bronchitis.

Moreover, chronic acid reflux, whether caused by GERD or LPR, can lead to a condition known as erosive esophagitis, in which the lining of the esophagus is inflamed and eroded away.

Accordingly, there is an ongoing need to develop pharmaceutical compositions and/or methods that are capable of treating acid reflux diseases including, but not limited to, GERD, LPR and erosive esophagitis. While many pharmaceutical compositions useful for treating GERD are known, there is an ongoing demand for new anti-reflux compositions.

Presently, there are no commercially available, approved medications for treating LPR specifically. All currently available reflux medications are directed to treating GERD.

Suggested management of LPR includes: following a bland diet (i.e., low acid levels, low in fat, not spicy); eating frequent, small meals; weight loss; avoiding alcohol, tobacco and caffeine; not eating within two hours before going to bed; and sleeping with the head and torso raised to prevent reflux into the throat. Accordingly, there is a need to develop pharmaceutical compositions and/or methods that are capable of treating LPR.

Existing drugs for treating GERD include H2 receptor antagonists and proton pump inhibitors.

H2 receptor antagonists (or "H2 blockers") were the first effective drugs for peptic ulcer and have been a mainstay of treatment for ulcers, GERD, and LPR.

In addition to affecting H1 receptors on the nasal mucosa, bronchi, and skin that participate in allergic reactions such as hay fever and hives, histamine also stimulates cells in the stomach lining to produce hydrochloric acid. H2 blockers compete with histamine for H2 receptors on the stomach's parietal cells, thereby leading to a decrease in production of hydrochloric acid. Acid-suppression lasts for several hours, allowing peptic ulcers to heal. Additionally, H2 blockers counteract the corrosive effects of refluxing acid.

However, unwanted side effects and possible interactions with other drugs are associated with H2 blockers. For example, safety has not been proven in pregnant women and H2 blockers appear in breast milk. Furthermore, H2 blockers are not the most effective drug for treating GERD, LPR, and other reflux diseases.

Presently, proton pump inhibitors are the most common modern pharmacologic class for treatment of hyperacidity and reflux associated therewith. They act by selectively blocking the $H^+$-$K^+$-ATPase enzyme of stomach parietal cells, resulting in a reduction in production of acid by stomach parietal cells. Examples of proton pump inhibitors used for treating reflux include omeprazole, lansoprazole, esomeprazole, pantoprazole, rabeprazole and the like.

Although, proton pump inhibitors are known to be effective in patients with GERD, LPR, and erosive esophagitis, and are among the most commonly recommended medications for treatment of acid reflux, proton pump inhibitors have been found to be unsuccessful in suppressing acid in some patients.

Moreover, proton pump inhibitors do not have immediate effect. Their effect is long because they necessarily have to be absorbed in order to exert their activity. Therefore, for example, absorption of omeprazole takes place in the small intestine and is completed within three to six hours. Furthermore, even after absorption has taken place, proton pump inhibitors may not begin working until as late as an additional 24 hours later. This behavior causes some technical inconveniencies for the design of a pharmaceutical composition.

Similarly, in several randomized, placebo-controlled trials of proton-pump inhibitors in the treatment of LPR, it has been found that a majority of patients with LPR experienced no significant benefit in symptom scores as compared to the placebo.

Suppression of gastric reflux should be effective against both vagally mediated throat clearing and coughing responses caused by irritation of the distal esophagus, and laryngeal injury caused by direct contact with erosive gastric refluxate. However, in the case of proton pump inhibitors, reflux is only modified by removal of its acid component, rather than prevented completely. Other damaging gastric reflux components such as pepsins and bile acids may still be present and active even in the absence of strong gastric acid.

SUMMARY

In an aspect, the disclosure provides for a pharmaceutical composition comprising, consisting of, or consisting essentially of:
- (i) one or more alginate salts, present in an amount from about 250 mg to about 2,000 mg,
- (ii) sodium bicarbonate, present in an amount from about 10 mg to about 100 mg, and
- (iii) calcium carbonate, present in an amount from about 10 mg to about 100 mg.

In an aspect, the disclosure provides for a pharmaceutical composition comprising, consisting of, or consisting essentially of:
- (i) one or more alginate salts, present in an amount from about 250 mg to about 2,000 mg, and
- (ii) sodium bicarbonate, present in an amount from about 10 mg to about 100 mg.

In an aspect, the disclosure provides for a pharmaceutical composition comprising, consisting of, or consisting essentially of:
- (i) one or more alginate salts, present in an amount from about 250 mg to about 2,000 mg, and
- (ii) calcium carbonate, present in an amount from about 10 mg to about 100 mg.

In an aspect, the disclosure provides for a pharmaceutical composition comprising, consisting of, or consisting essentially of one or more alginate salts, present in an amount from about 250 mg to about 2,000 mg.

In an aspect, the alginate salt comprises sodium alginate.

In another aspect, pharmaceutical compositions described herein further comprise (iv) citric acid in an amount from about 10 mg to about 1000 mg. In an optional aspect, the pharmaceutical composition further comprises (v) one or more natural or artificial sweetener or flavorants, present in an amount from about 10 mg to about 2000 mg. In yet another aspect, the (v) one or more natural or artificial sweetener or flavorants comprises stevia extract.

The disclosure provides for aspects where the compositions described herein are in the form of a capsule, tablet, or powder. In an aspect, the composition is not in the form of tablet and only in the form of a capsule and/or powder formulations.

In an aspect, the alginate salt comprises sodium alginate present in an amount selected from the group consisting of from about 250 mg to about 2000 mg, from about 300 mg to about 1300 mg, from about 800 to about 1200 mg, from about 500 to about 1000 mg, from about 300 mg to about 700 mg, and from about 400 mg to about 600 mg.

In yet another aspect, the sodium bicarbonate is present in an amount selected from the group consisting of from about 10 mg to about 100 mg, from about 20 mg to about 80 mg, from about 30 to about 70 mg, and from about 40 to about 60 mg.

The disclosure further provides for aspects wherein the calcium carbonate is present in an amount selected from the group consisting of from about 10 mg to about 100 mg, from about 20 mg to about 80 mg, from about 30 to about 70 mg, and from about 40 to about 60 mg.

In another aspect, pharmaceutical compositions described herein are in the form of a capsule and consists of:
- (i) one or more alginate salts, present in an amount from about 400 mg to about 750 mg,
- (ii) sodium bicarbonate, present in an amount from about 20 mg to about 40 mg, and
- (iii) calcium carbonate, present in an amount from about 30 mg to about 50 mg.

In yet another aspect, pharmaceutical compositions described herein are in the form of a powder and consists of:
- (i) one or more alginate salts, present in an amount from about 800 mg to about 1200 mg,
- (ii) sodium bicarbonate, present in an amount from about 30 mg to about 70 mg, and
- (iii) calcium carbonate, present in an amount from about 50 mg to about 70 mg;
- (iv) citric acid, present in an amount from about 400 mg to about 600 mg, and
- (v) optionally one or more natural or artificial sweetener or flavorants, present in an amount from about 400 mg to about 600 mg.

The disclosure further provides methods of treating individuals or patients with a composition or dosage form described herein.

In an aspect, the pharmaceutical composition is administered 1, 2, 3, 4, 5, 6, 7, 8, 9, or 10 times per day to a patient in need thereof. In another aspect, the pharmaceutical composition is administered in a dose of two capsules at a rate of two, three, or four times daily to a patient in need thereof.

In an aspect, the individual or patient in need thereof has or has been diagnosed with acid reflux. In another aspect, the acid reflux disease is selected from the group consisting of gastroesophageal reflux disease, laryngopharyngeal reflux, and erosive esophagitis.

In an aspect, the acid reflux disease is not gastroesophageal reflux disease.

In yet another aspect, the acid reflux disease is not gastroesophageal reflux disease and only patients diagnosed with laryngopharyngeal reflux are treated.

The present invention provides for novel pharmaceutical composition formulations useful for treating acid reflux diseases including, but not limited to, GERD, LPR, and erosive esophagitis, wherein such compositions comprise as an active ingredient one or more alginate, preferably sodium alginate.

It has been found that compositions comprising sodium alginate as an active ingredient are effective and rapid in controlling buildup and reflux of stomach acid associated with acid reflux diseases.

The disclosure further provides for methods of treating acid reflux diseases comprising administering a pharmaceutical composition which comprises one or more alginate, preferably sodium alginate.

DETAILED DESCRIPTION

Applicants have found that alginate-containing compositions successfully treat and prevent acid reflux diseases, even in the absence of proton pump inhibitors and H2 blockers. To date, pharmaceutical compositions comprising proton pump inhibitors or H2 blockers as active ingredients have been preferred for treating reflux diseases.

The post-prandial acid pocket is an area of unbuffered gastric acid that accumulates in the proximal stomach following meals and which serves as a reservoir for acid reflux in both healthy individuals and acid reflux patients. The acid pocket it thus an attractive target for reflux treatment.

Alginates treat reflux diseases via a unique mechanism by creating a mechanical barrier, or raft, in the fundus of the stomach, which displaces the acid pocket in the proximal stomach. Although increasing evidence indicates that alginates displace the post-prandial acid pocket and thus inhibit acid exposure in the esophagus.

When alginates come into contact with gastric acid, a mechanical foam barrier is formed. The resulting barrier physically prevents any refluxing acid from ascending into the esophagus or pharynx. The foam barrier can last for several hours, allowing for prolonged relief from reflux symptoms.

Specifically, when sodium alginate comes into contact with gastric acid, alginic acid is formed, which is an insoluble linear polymer.

Preferably, an alginic acid raft that persists for a prolonged period can be formed by adding components such as sodium bicarbonate and calcium carbonate.

The addition of sodium bicarbonate allows for a reaction between gastric acid and sodium bicarbonate, which gives off carbon dioxide. The carbon dioxide gas driven off by this reaction aids in lifting the raft to the surface of the stomach contents where the raft can prevent reflux.

The addition of calcium carbonate provides a further source of carbon dioxide, as well as a source of calcium ions. Calcium ions are useful for cross-linking the alginic acid polymer formed by reacting sodium alginate with gastric acid, thereby stabilizing the alginic acid raft for prolonged reflux relief.

Prolonged stabilization of the alginic acid raft is preferred as the raft is gradually broken up over time mechanically by stomach contractions.

By providing an impediment to distal esophageal acid exposure, alginates are a promising class for treatment and prevention of acid reflux diseases, especially for individuals who do not respond to anti-secretory therapies such as proton pump inhibitors or H2 blockers.

As compared to proton pump inhibitors and H2 blockers, alginates have been found to provide superior benefit over antacids and could be considered as an initial treatment for patients, in particular for patients for whom chronic acid suppression is either undesirable or unnecessary.

Unlike proton pump inhibitors, which require absorption over the course of three to six hours and may take up to an additional 24 hours to work, alginates show immediate effect. Control of hyperacidity by alginates is rapid as they act in the stomach, not the small intestine, and require no prior absorption.

To date, alginates have been incorporated only as inactive ingredients and the medical and pharmaceutical communities have favored usage of proton pump inhibitors and/or H2 blockers.

However, Applicants have found that alginates provide a promising alternative for reflux treatment as active ingredients.

The disclosure provides for pharmaceutical compositions comprising as active ingredients one or more alginates.

In an aspect, the pharmaceutical composition of the present invention comprises one or more alginates as an active ingredient in an amount from about 1.0 mg to about 10,000 mg, or from about 5.0 mg to about 5,000 mg, or from about 10 mg to about 2,500 mg, or from about 100 mg to about 1,000 mg, depending on the severity of the condition being treated, the nature of the oral formulation and the age, weight and condition of the patient.

In a preferred embodiment of the invention, the active ingredient is sodium alginate.

In an embodiment, the pharmaceutical composition of the present invention further comprises sodium bicarbonate.

Sodium bicarbonate is a known antacid. As a component of the present invention, sodium bicarbonate is useful in neutralizing the gastric acid beneath the foam barrier formed by sodium alginate coming into contact with the gastric acid. Thus, the mechanism of this embodiment of the present invention is two-fold, comprising the formation of a mechanical barrier to prevent reflux, and further comprising the neutralization of the acid contained by the foam barrier.

Additionally, reaction of sodium bicarbonate with gastric acid produces carbon dioxide gas, which assists in lifting the alginic acid raft to the stomach contents' surface.

In an aspect, the pharmaceutical composition of the present invention comprises sodium bicarbonate in an amount from about 1.0 mg to about 1,000 mg, or from about 5.0 mg to about 500 mg, or from about 10 mg to about 100 mg, or from about 25 mg to about 75 mg.

In an embodiment, the pharmaceutical composition of the present invention further comprises calcium carbonate.

Calcium carbonate is a known antacid. Thus, like embodiments comprising sodium bicarbonate, embodiments of the present invention comprising calcium carbonate are useful for neutralizing increased acidity in the stomach. Additionally, reaction of calcium carbonate with gastric acid produces carbon dioxide gas, which assists in lifting the alginic acid raft to the stomach contents' surface.

In an aspect, the pharmaceutical composition of the present invention comprises calcium carbonate in an amount from about 1.0 mg to about 1,000 mg, or from about 5.0 mg to about 500 mg, or from about 10 mg to about 100 mg, or from about 25 to about 75 mg.

In an embodiment, the pharmaceutical composition of the present invention further comprises citric acid.

As a component of the present invention, citric acid is used to enhance the flavor of powder formulations, which optionally may comprise further flavorants and/or sweeteners.

Furthermore, the citric acid and sodium bicarbonate components react to cause an effervescent effect whereby carbon dioxide bubbles are produced when the powder formulation is dissolved in water.

In an aspect, the pharmaceutical composition of the present invention comprises citric acid in an amount from about 1.0 mg to about 10,000 mg, or from about 10 mg to about 5,000 mg, or from about 100 mg to about 1,000 mg, or from about 250 mg to about 750 mg.

In an aspect, the pharmaceutical composition of the present invention comprises one or more natural or artificial sweeteners, such as stevia extract, sucrose, acesulfame potassium, aspartame, neotame, saccharin, sucralose, sorbitol, xylitol, mannitol.

In an aspect, the pharmaceutical composition of the present invention comprises one or more natural or artificial flavorants. Natural flavorants include, but are not limited to, essential oils, oleoresin, essence or extractive, protein hydrolysate, distillate, or any product of roasting, heating or enzymolysis, which contains the flavoring constituents derived from a spice, fruit or fruit juice, vegetable or vegetable juice, edible yeast, herb, bark, bud, root, leaf or similar plant material, meat, seafood, poultry, eggs, dairy products, or fermentation products thereof, whose significant function in food is flavoring rather than nutritional.

Artificial flavorants include, but are not limited to, any substance, the function of which is to impart flavor, which is not derived from a spice, fruit or fruit juice, vegetable or vegetable juice, edible yeast, herb, bark, bud, root, leaf or similar plant material, meat, fish, poultry, eggs, dairy products, or fermentation products thereof.

In one embodiment, the pharmaceutical composition of the present invention comprises stevia extract.

In an embodiment, the pharmaceutical composition of the present invention further comprises an artificial or natural sweetener or flavorant.

In an aspect, the pharmaceutical composition of the present invention comprises an artificial or natural sweetener or flavorant in an amount from about 1.0 mg to about 10,000 mg, or from about 10 mg to about 5,000 mg, or from about 100 mg to about 1,000 mg, or from about 250 mg to about 750 mg.

The disclosure further provides for methods of treatment of acid reflux diseases.

In one embodiment, the disclosure provides for a method of treating acid reflux diseases comprising administering a pharmaceutical composition in a capsule dosage form.

Each capsule dosage according to the claimed method is may ultimately be at the discretion of an attendant physician or may be within a pre-defined range for self-administration by the patient.

In an aspect, the capsule dosage according to the claimed method is two capsules. The method allows for administration of up to three doses daily, as needed, preferably following meals.

In an aspect, the composition of the present invention, as either a capsule or powder dosage form, may be administered alone. In another aspect, the composition of the present invention may be administered in combination with a proton pump inhibitor medication to enhance the proton pump inhibitor's effect.

In another embodiment, the disclosure provides for a method of treating acid reflux diseases comprising administering a pharmaceutical composition in a powder dosage form.

Each powder dosage according to the claimed method is may ultimately be at the discretion of an attendant physician or may be within a pre-defined range for self-administration by the patient.

In an aspect, the powder dosage according to the claimed method is dissolved in one-quarter cup of water. The method allows for administration of up to three doses daily, as needed, preferably following meals.

In an aspect, pharmaceutical compositions of the present invention are effective for protection of the stomach and intestine and for treating gastrointestinal disorders including, but not limited gastroesophageal reflux disease, laryngopharyngeal reflux, erosive esophagitis, and other acid reflux diseases.

In an aspect, the individual or patient in need thereof has or has been diagnosed with acid reflux. In another aspect, the acid reflux disease is selected from the group consisting of gastroesophageal reflux disease, laryngopharyngeal reflux, and erosive esophagitis.

In an aspect, the acid reflux disease is not gastroesophageal reflux disease.

In yet another aspect, the acid reflux disease is not gastroesophageal reflux disease and only patients diagnosed with laryngopharyngeal reflux are treated.

Suitable formulations and dosage forms of the present invention include, but are not limited to, powders, hard capsules, soft capsules, pills, suppositories, gels, and compressed tablets manufactured from a pharmaceutical composition of the present invention. The dosage forms can be any shape, including regular or irregular shapes. These formulations may be prepared by methods known in the art, e.g., by means of conventional pan-coating, mixing, granulation or lyophilization processes.

Solid dosage forms for oral administration (capsules, tablets, pills, dragees, powders, granules and the like) may be prepared, e.g., by mixing the active ingredient(s) with one or more pharmaceutically-acceptable carriers and, optionally, one or more fillers, extenders, binders, humectants, disintegrating agents, solution retarding agents, absorption accelerators, wetting agents, absorbents, lubricants, and/or coloring agents. Solid compositions of a similar type maybe employed as fillers in soft and hard-filled gelatin capsules using a suitable excipient. A tablet may be made by compression or molding, optionally with one or more accessory ingredients. Compressed tablets may be prepared using a suitable binder, lubricant, inert diluent, preservative, disintegrant, surface-active or dispersing agent. Molded tablets may be made by molding in a suitable machine. The tablets, and other solid dosage forms, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein. They may be sterilized by, for example, filtration through a bacteria-retaining filter. These compositions may also optionally contain opacifying agents and may be of a composition such that they release the active ingredient only, or preferentially, in a certain portion of the gastrointestinal tract, optionally, in a delayed manner. The active ingredient can also be in microencapsulated form.

A pharmaceutical composition of the present invention may be administered in any desired and effective manner. Further, a pharmaceutical composition of the present invention may be administered in conjunction with other treatments. A pharmaceutical composition of the present invention maybe encapsulated or otherwise protected against gastric or other secretions, if desired.

In an aspect, the pharmaceutical composition is in a unit dosage form.

In an embodiment, the unit dosage form is a capsule.

In an aspect, the pharmaceutical composition of the present invention is administered in a hard-shell (i.e., two-piece) capsule.

In another aspect, the pharmaceutical composition of the present invention is administered in a soft-shell (i.e., single-piece) capsule.

The capsule dosage form may be of any standard size, selected from the sizes 5, 4, 3, 2, 1, 0, 0E, 00, 00E, 000, 13, 12, 12e1, 11, 10, 7, and Su07.

In an aspect, the capsule dosage form is a hard-shell capsule of size 0, 0E, 00, 00E, 000 or 1.

In an aspect, the capsule dosage form is a hard-shell capsule of size 00.

In an aspect, the capsule dosage form is a rapid-release capsule.

Rapid release of the active ingredient is preferred. If the active ingredient (e.g., the alginate salt) is released too slowly, reflux of stomach acid into the pharynx can cause digestion of the dosage form (e.g., the capsule) before the active ingredient can take effect (e.g., form an alginate raft).

In another embodiment, the pharmaceutical composition of the present invention is a dry powder.

As used herein, the term "acid reflux disease" means any disease or condition characterized by stomach contents coming back up, or refluxing, into the esophagus resulting in symptoms or complications, including the taste of acid in the back of the mouth, heartburn, bad breath, chest pain, vomiting, burping, dyspepsia, respiratory problems, erosion of the teeth, esophagitis, esophageal strictures, and Barrett's esophagus.

As used herein, the terms "treat," "treating," "treatment" and grammatical variations thereof mean subjecting an individual subject to a protocol, regimen, process or remedy, in which it is desired to obtain a physiologic response or outcome in that subject, e.g., a patient. In particular, the methods and compositions of the present invention may be used to slow the development of disease symptoms or delay the onset of the disease or condition, or halt the progression of disease development. However, because every treated subject may not respond to a particular treatment protocol, regimen, process or remedy, treating does not require that the desired physiologic response or outcome be achieved in each and every subject or subject, e.g., patient, population. Accordingly, a given subject or subject, e.g., patient, population may fail to respond or respond inadequately to treatment.

As used herein, the terms "ameliorate", "ameliorating" and grammatical variations thereof mean to decrease the severity of the symptoms of a disease in a subject.

As used herein, the terms "prevent", "preventing" and grammatical variations thereof mean to administer a compound or composition of the present invention to a subject who has not been diagnosed as having the disease or condition at the time of administration, but who could be expected to develop the disease or condition or be at increased risk for the disease or condition. Preventing also includes administration of at least one compound or a composition of the present invention to those subjects thought to be predisposed to the disease or condition due to age, familial history, genetic or chromosomal abnormalities, due to the presence of one or more biological markers for the disease or condition and/or due to environmental factors.

As used herein, the term "gastrointestinal disorder" encompasses any infection, disease or other disorder(s) of the upper gastrointestinal tract. Such disorders include, for example, heartburn; sour stomach; acid ingestion; upset stomach and/or pain associated with heartburn, sour stomach and acid ingestion; bloating; fullness; dyspepsia; hiatus hernia; esophagitis; nocturnal heartburn; erosive esophagitis; disorders not manifested by the presence of ulcerations in the gastric mucosa, including chronic active or atrophic gastritis, Zollinger-Ellison syndrome; non-ulcer dyspepsia, esophageal reflux disease and gastric motility disorders; peptic ulcer disease, i.e., pre-pyloric, marginal, and/or gastric, duodenal ulcers; and combinations thereof. Preferred for treatment by the present invention includes heartburn with and without stomach pain, dyspepsia, esophagitis, chronic active or atrophic gastritis and esophageal reflux disease.

As used herein, the term "protection of the stomach and intestine" means the prevention and/or treatment of gastrointestinal diseases, in particular those which are non-cancerous in origin, especially gastrointestinal inflammatory diseases and lesions (such as, for example, gastric ulcer, duodenal ulcer, gastritis and stomach irritation caused by hyperacidity or medicaments), which can be caused, for example, by microorganisms, bacterial toxins, medicaments (for example certain anti-inflammatories and antirheumatics), other chemicals (for example ethanol), gastric acid or stress situations.

As used herein, the terms "effective amount" or "therapeutically effective amount" mean an amount of the active ingredient or an amount of the composition according to the invention is an amount thereof that is sufficient to effect beneficial or desired results as described herein when administered to a subject. Effective dosage forms, modes of administration, and dosage amounts may be determined empirically, and making such determinations is within the skill of the art. It is understood by those skilled in the art that the dosage amount will vary with the route of administration, the rate of excretion, the duration of the treatment, the identity of any other drugs being administered, the age, size, and species of mammal, e.g., human patient, and like factors well known in the arts of medicine and veterinary medicine. In general, a suitable dose of the composition according to the invention will be that amount of the composition, which is the lowest dose effective to produce the desired effect with no or minimal side effects. The effective dose of composition may be administered as two, three, four, five, six or more sub-doses, administered separately at appropriate intervals throughout the day, with the proviso that the doses of the composition simultaneously ameliorate or prevent reflux symptoms.

The pharmaceutical compositions of the invention are pharmaceutically acceptable and comprise one or more active ingredients in admixture with one or more pharmaceutically-acceptable carriers and, optionally, one or more other compounds, drugs, ingredients and/or materials. Regardless of the route of administration selected, the agents/compounds of the present invention are formulated into pharmaceutically-acceptable dosage forms by conventional methods known to those of skill in the art. See, e.g., Remington, The Science and Practice of Pharmacy (21.sup.st Edition, Lippincott Williams and Wilkins, Philadelphia, Pa.).

In an aspect, the pharmaceutical composition of the present invention does not comprise a proton pump inhibitor.

As used herein, the term "proton pump inhibitor" means any agent within the class of antisecretory compounds, which suppress gastric acid secretion by irreversible inhibition of the H+/K+ ATPase enzyme system at the secretory surface of the parietal cell.

In an aspect, the pharmaceutical composition of the present invention does not comprise an H2 blocker.

As used herein, the term "H2 blocker" means any agent within the class of antisecretory compounds, which suppress the normal secretion of gastric acid by parietal cells and the meal-stimulated secretion of acid by blocking the binding of histamine to H2 receptors in parietal cells in the lining of the fundus and the body of the stomach.

In an aspect, the pharmaceutical composition of the present invention comprises one or more pharmaceutically acceptable excipients.

As used herein, a "pharmaceutically acceptable" component is one that is suitable for use with humans and/or animals without undue adverse side effects (such as toxicity, irritation, and allergic response) commensurate with a reasonable benefit/risk ratio.

As used herein, the term "excipient" means any component of an oral dosage form that is not an active pharmaceutical ingredient (i.e., sodium alginate). Excipients include, but are not limited to, binders, lubricants, diluents, disintegrants, coatings, barrier layer components, glidants, and other components. Excipients are known in the art (see HANDBOOK OF PHARMACEUTICAL EXCIPIENTS, FIFTH EDITION, 2005, edited by Rowe et al., McGraw Hill). Some excipients may serve multiple functions or are so-called high functionality excipients.

Pharmaceutically acceptable carriers are well known in the art (see, e.g., Remington, The Science and Practice of Pharmacy (21.sup.st Edition, Lippincott Williams and Wilkins, Philadelphia, Pa.) and The National Formulary (American Pharmaceutical Association, Washington, D.C.)) and include sugars (e.g., lactose, sucrose, mannitol, and sorbitol), starches, cellulose preparations, calcium phosphates (e.g., dicalcium phosphate, tricalcium phosphate and calcium hydrogen phosphate), sodium citrate, water, aqueous solutions (e.g., saline, sodium chloride injection, Ringer's injection, dextrose injection, dextrose and sodium chloride injection, lactated Ringer's injection), alcohols (e.g., ethyl alcohol, propyl alcohol, and benzyl alcohol), polyols (e.g., glycerol, propylene glycol, and polyethylene glycol), organic esters (e.g., ethyl oleate and tryglycerides), biodegradable polymers (e.g., polylactide-polyglycolide, poly(orthoesters), and poly(anhydrides)), elastomeric matrices, liposomes, microspheres, oils (e.g., corn, germ, olive, castor, sesame, cottonseed, and groundnut), cocoa butter, waxes (e.g., suppository waxes), paraffins, silicones, talc, silicylate, etc. Each pharmaceutically acceptable carrier used in a pharmaceutical composition of the invention must be "acceptable" in the sense of being compatible with the other ingredients of the formulation and not injurious to the subject. Carriers suitable for a selected dosage form and intended route of administration are well known in the art, and acceptable carriers for a chosen dosage form and method of administration can be determined using ordinary skill in the art.

The pharmaceutical compositions of the invention may, optionally, contain additional ingredients and/or materials commonly used in such pharmaceutical compositions. These ingredients and materials are well known in the art and include (1) fillers or extenders, such as starches, lactose, sucrose, glucose, mannitol, and silicic acid; (2) binders, such as carboxymethylcellulose, alginates, gelatin, polyvinyl pyrrolidone, hydroxypropylmethyl cellulose, glucose, sucrose, acacia, compressible sugar (e.g., NuTab), cellulose, methylcellulose, ethylcellulose, povidone and pregelatinized starch; (3) humectants, such as glycerol; (4) disintegrating agents, such as agar-agar, potato or tapioca starch, corn starch, pre-gelatinized and modified starches, clays such as bentonite, alginates, alginic acid, certain silicates, sodium starch glycolate, methyl cellulose, cross-linked sodium carboxymethyl cellulose, microcrystalline cellulose (e.g., Avicel), sodium carbonate, calcium carbonate, hydroxy propylcellulose-low substituted, colloidal silicon dioxide, cellulose polyacrilin potassium (e.g., Amberlite), gums, guar, locust bean, karaya, xanthan, pectin, tragacanth, and polyvinylpyrrolidone; (5) solution retarding agents, such as paraffin; (6) absorption accelerators, such as quaternary ammonium compounds; (7) wetting agents, such as cetyl alcohol and glycerol monostearate; (8) absorbents, such as kaolin and bentonite clay; (9) lubricants, such as sodium oleate, sodium stearate, calcium stearate, zinc stearate, magnesium stearate, polyethylene glycol, talc, mineral oil, stearic acid, sodium benzoate, sodium acetate, sodium chloride, and sodium lauryl sulfate; (10) suspending agents, such as ethoxylated isostearyl alcohols, polyoxyethylene sorbitol and sorbitan esters, microcrystalline cellulose, aluminum metahydroxide, bentonite, agar-agar and tragacanth; (11) buffering agents, such as potassium metaphosphate, potassium phosphate, monobasic sodium acetate and sodium citrate anhydrous and dihydrate; (12) excipients, such as lactose, milk sugars, polyethylene glycols, animal and vegetable fats, oils, waxes, paraffins, cocoa butter, starches, tragacanth, cellulose derivatives, polyethylene glycol, silicones, bentonites, silicic acid, talc, salicylate, zinc oxide, aluminum hydroxide, calcium silicates, and polyamide powder; (13) inert diluents, such as dibasic calcium phosphate, kaolin, lactose, dextrose, magnesium carbonate, sucrose, mannitol, microcrystalline cellulose, powdered cellulose, precipitated calcium carbonate, calcium sulfate, sorbitol, starch, and water or other solvents; (14) preservatives, such as Nipagin, Nipasol, alcohol, antimicrobial agents, benzoic acid, sodium benzoate, benzyl alcohol, sorbic acid, parabens, and isopropyl alcohol ; (15) surface-active agents; (16) dispersing agents, such as synthetic and natural gums including tragacanth, acacia, alginate, dextran, sodium carboxymethylcellulose, methylcellulose, polyvinylpyrrolidone and gelatin; (17) control-release or absorption-delaying agents, such as hydroxypropylmethyl cellulose, other polymer matrices, biodegradable polymers, liposomes, microspheres, aluminum monosterate, gelatin, and waxes; (18) opacifying agents; (19) adjuvants; (20) wetting agents; (21) emulsifying and suspending agents; (22), solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan; (23) propellants, such as chlorofluorohydrocarbons and volatile unsubstituted hydrocarbons, such as butane and propane; (24) antioxidants, such as ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate and sodium metabisulfite; (25) agents which render the formulation isotonic with the blood of the intended recipient, such as sugars and sodium chloride; (26) thickening agents; (27) coating materials, such as lecithin; and (28) sweetening, flavoring, coloring, perfuming and preservative agents. Each such ingredient or material must be "acceptable" in the sense of being compatible with the other ingredients of the formulation and not injurious to the subject. Ingredients and materials suitable for a selected dosage form and intended route of administration are well known in the art, and acceptable ingredients and materials for a chosen dosage form and method of administration may be determined using ordinary skill in the art.

The following examples serve to illustrate certain aspects of the disclosure and are not intended to limit the disclosure.

EXAMPLES

Example 1—Capsule Formulation

The formulation of this Example provides for representative pharmaceutical formulations in, for example, capsules. A representative formulation per capsule includes, for example:
  i. 500 mg sodium alginate;
  ii. 25 mg sodium bicarbonate; and
  iii. 35 mg calcium carbonate The formulation may be formulated in a standard 00 sized hard-shell capsule. Two capsules (as a dose) may be administered to a patient in need thereof three times daily (for a total of six capsules per day).

Example 2—Capsule Formulation

The formulation of this Example provides for representative pharmaceutical formulations in, for example, capsules. A representative formulation per capsule includes, for example:
  i. 550 mg sodium alginate;
  ii. 10 mg sodium bicarbonate; and
  iii. 10 mg calcium carbonate The formulation may be formulated in a standard 00 sized hard-shell capsule. Two capsules (as a dose) may be administered to a patient in need thereof three times daily (for a total of six capsules per day).

Example 3—Capsule Formulation

The formulation of this Example provides for representative pharmaceutical formulations in, for example, capsules. A representative formulation per capsule includes, for example:
  i. 250 mg sodium alginate;
  ii. 12.5 mg sodium bicarbonate; and
  iii. 17.5 mg calcium carbonate The formulation may be formulated in a standard 1 sized hard-shell capsule. Two capsules (as a dose) may be administered to a patient in need thereof three times daily (for a total of six capsules per day).

Example 4—Capsule Formulation

The formulation of this Example provides for representative pharmaceutical formulations in, for example, capsules. A representative formulation per capsule includes, for example:
  i. 400 mg sodium alginate;
  ii. 20 mg sodium bicarbonate; and
  iii. 30 mg calcium carbonate The formulation may be formulated in a standard 0 sized hard-shell capsule. Two capsules (as a dose) may be administered to a patient in need thereof three times daily (for a total of six capsules per day).

Example 5—Capsule Formulation

The formulation of this Example provides for representative pharmaceutical formulations in, for example, capsules. A representative formulation per capsule includes, for example:
  i. 600 mg sodium alginate;
  ii. 50 mg sodium bicarbonate; and
  iii. 70 mg calcium carbonate The formulation may be formulated in a standard 00E sized hard-shell capsule. Two capsules (as a dose) may be administered to a patient in need thereof three times daily (for a total of six capsules per day).

Example 6—Powder Formulation

The formulation of this Example provides for representative pharmaceutical formulations in, for example, powder form. A representative formulation powder formulation includes, for example:
  i. 1,000 mg sodium alginate;
  ii. 50 mg sodium bicarbonate;
  iii. 70 mg calcium carbonate;
  iv. 500 mg citric acid; and
  v. 500 mg artificial or natural sweetener, optionally stevia extract The formulation may be formulated in a dry powder to be mixed with one-quarter cup of water and swallowed. A dose may be administered to a patient in need thereof up to three times daily.

Example 7—Powder Formulation

The formulation of this Example provides for representative pharmaceutical formulations in, for example, powder form. A representative formulation powder formulation includes, for example:
  i. 100 mg sodium alginate;
  ii. 5 mg sodium bicarbonate;
  iii. 7 mg calcium carbonate;
  iv. 50 mg citric acid; and
  v. 50 mg artificial or natural sweetener, optionally stevia extract The formulation may be formulated in a dry powder to be mixed with one-quarter cup of water and swallowed. A dose may be administered to a patient in need thereof up to three times daily.

Example 8—Powder Formulation

The formulation of this Example provides for representative pharmaceutical formulations in, for example, powder form. A representative formulation powder formulation includes, for example:
  i. 500 mg sodium alginate;
  ii. 25 mg sodium bicarbonate;
  iii. 35 mg calcium carbonate;
  iv. 250 mg citric acid; and
  v. 500 mg artificial or natural sweetener, optionally stevia extract The formulation may be formulated in a dry powder to be mixed with one-quarter cup of water and swallowed. A dose may be administered to a patient in need thereof up to three times daily.

Example 9—Powder Formulation

The formulation of this Example provides for representative pharmaceutical formulations in, for example, powder form. A representative formulation powder formulation includes, for example:
  i. 1,200 mg sodium alginate;
  ii. 70 mg sodium bicarbonate;
  iii. 90 mg calcium carbonate;
  iv. 500 mg citric acid; and
  v. 500 mg artificial or natural sweetener, optionally stevia extract The formulation may be formulated in a dry powder to be mixed with one-quarter cup of water and swallowed. A dose may be administered to a patient in need thereof up to three times daily.

Example 10—Powder Formulation

The formulation of this Example provides for representative pharmaceutical formulations in, for example, powder form. A representative formulation powder formulation includes, for example:

i. 200 mg sodium alginate;
ii. 10 mg sodium bicarbonate;
iii. 14 mg calcium carbonate;
iv. 20 mg citric acid; and
v. 20 mg artificial or natural sweetener, optionally stevia extract The formulation may be formulated in a dry powder to be mixed with one-quarter cup of water and swallowed. A dose may be administered to a patient in need thereof up to three times daily.

Example 11—Powder Formulation

The formulation of this Example provides for representative pharmaceutical formulations in, for example, powder form. A representative formulation powder formulation includes, for example:
i. 300 mg sodium alginate;
ii. 15 mg sodium bicarbonate;
iii. 20 mg calcium carbonate;
iv. 30 mg citric acid; and
v. 30 mg artificial or natural sweetener, optionally stevia extract The formulation may be formulated in a dry powder to be mixed with one-quarter cup of water and swallowed. A dose may be administered to a patient in need thereof up to three times daily.

Example 12—Powder Formulation

The formulation of this Example provides for representative pharmaceutical formulations in, for example, powder form. A representative formulation powder formulation includes, for example:
i. 750 mg sodium alginate;
ii. 25 mg sodium bicarbonate;
iii. 35 mg calcium carbonate;
iv. 250 mg citric acid; and
v. 500 mg artificial or natural sweetener, optionally stevia extract The formulation may be formulated in a dry powder to be mixed with one-quarter cup of water and swallowed. A dose may be administered to a patient in need thereof up to three times daily.

Example 13—Powder Formulation

The formulation of this Example provides for representative pharmaceutical formulations in, for example, powder form. A representative formulation powder formulation includes, for example:
i. 750 mg sodium alginate;
ii. 25 mg sodium bicarbonate;
iii. 35 mg calcium carbonate;
iv. 500 mg citric acid; and
v. 500 mg artificial or natural sweetener, optionally stevia extract The formulation may be formulated in a dry powder to be mixed with one-quarter cup of water and swallowed. A dose may be administered to a patient in need thereof up to three times daily.

The invention claimed is:

1. A method of treating acid reflux disease in an individual in need thereof, comprising administering to an individual in need thereof a pharmaceutical composition formulated as a powder consisting of:
   (i) one or more alginate salts, present in an amount from about 30% to 78% wt of the pharmaceutical composition,
   (ii) sodium bicarbonate, present in an amount from about 1% to 10% wt of the pharmaceutical composition,
   (iii) calcium carbonate, present in an amount from about 1% to 10% wt of the pharmaceutical composition,
   (iv) citric acid, present in an amount from about 21% to 30% wt of the pharmaceutical composition,
   (v) optionally one or more natural or artificial sweetener or flavorants; and
   dissolving the powder form in liquid prior to administration to individual and wherein the composition forms alginate raft prior to administering to an individual.

2. The method of claim 1, wherein the alginate salt comprises sodium alginate.

3. The method of claim 1, wherein the citric acid is present in an amount from about 22% to 29% wt, about 23% to 28% wt, or about 24% to 27% wt.

4. The method of claim 1, wherein the (v) one or more natural or artificial sweetener or flavorants are present in an amount from about 1% to 40% wt of the pharmaceutical composition.

5. The method of claim 4, wherein the (v) one or more natural or artificial sweetener or flavorants comprises stevia extract.

6. The method of claim 4, wherein said pharmaceutical composition consists of:
   (i) one or more alginate salts, present in an amount from about 30% to 50% wt of the pharmaceutical composition,
   (ii) sodium bicarbonate, present in an amount from about 1% to 5% wt of the pharmaceutical composition,
   (iii) calcium carbonate, present in an amount from about 1% to 5% wt of the pharmaceutical composition,
   (iv) citric acid, present in an amount from about 21% to 30% wt of the pharmaceutical composition,
   (v) optionally one or more natural or artificial sweetener or flavorants, and dissolving the powder form in liquid prior to administration to individual, and wherein the composition forms alginate raft prior to administering to an individual.

7. The method of claim 4, wherein said pharmaceutical composition consists of:
   (i) one or more alginate salts, present in an amount from about 51% to 75% wt of the pharmaceutical composition,
   (ii) sodium bicarbonate, present in an amount from about 1% to 5% wt of the pharmaceutical composition,
   (iii) calcium carbonate, present in an amount from about 1% to 5% wt of the pharmaceutical composition,
   (iv) citric acid, present in an amount from about 21% to 30% wt of the pharmaceutical composition,
   (v) optionally one or more natural or artificial sweetener or flavorants, and dissolving the powder form in liquid prior to administration to individual, and wherein the composition forms alginate raft prior to administering to an individual.

8. The method of claim 1, wherein the alginate salt comprises sodium alginate present in an amount 35% to 75% wt, 40% to 70% wt, 45% to 65% wt, or 50% to 60% wt.

9. The method of claim 1, wherein the sodium bicarbonate is present in an amount from about 1% to 10% wt, 2% to 9% wt, 3% to 8% wt, or 4% to 7% wt.

10. The method of claim 1, wherein the calcium carbonate is present in an amount 1% to 10% wt, 2% to 9% wt, 3% to 8% wt, or 4% to 7% wt.

11. The method according to claim 1, wherein the pharmaceutical composition is administered 1, 2, 3, 4, 5, 6, 7, 8, 9, or 10 times per day to a patient in need thereof.

12. The method according to claim 1, wherein the powder form is dissolved in one-quarter or half cup of water prior to administration to individual.

13. The method according to claim 1, wherein the acid reflux disease is selected from the group consisting of gastroesophageal reflux disease, laryngopharyngeal reflux, and erosive esophagitis.

14. The method according to claim 1, wherein the acid reflux disease is gastroesophageal reflux disease.

15. The method according to claim 1, wherein the acid reflux disease is laryngopharyngeal reflux.

16. The method according to claim 1, wherein the acid reflux disease is erosive esophagitis.

17. The method according to claim 1, wherein the acid reflux disease is not gastroesophageal reflux disease.

18. The method according to claim 1, wherein the acid reflux disease is not gastroesophageal reflux disease and only patients diagnosed with laryngopharyngeal reflux are treated.

19. The method according to claim 1, further comprising treating at least one symptom of acid reflux disease in an individual in need thereof, wherein the at least one symptom of acid reflux disease is selected from a group consisting of vagally mediated throat clearing and coughing responses caused by irritation of the distal esophagus, and laryngeal injury caused by direct contact with erosive gastric refluxate.

20. The method of claim 1, wherein the composition gels and foams prior to administering to an individual.

21. The method of claim 1, wherein the composition does not include polyols.

* * * * *